(12) United States Patent
Kulkarni et al.

(10) Patent No.: US 6,897,320 B2
(45) Date of Patent: May 24, 2005

(54) PROCESS FOR PREPARING 2,6-DIVINYLPYRIDINE AND 2-METHYL-6-VINYLPYRIDINE FROM 2,6-LUTIDINE OVER MODIFIED ZEOLITES

(75) Inventors: Shivanand Janardan Kulkarni, Andhra Pradesh (IN); Madhavi Gangapuram, Andhra Pradesh (IN); Vijaya Raghavan Kondapuram, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 58 days.

(21) Appl. No.: 10/395,852

(22) Filed: Mar. 25, 2003

(65) Prior Publication Data

US 2004/0192925 A1 Sep. 30, 2004

(51) Int. Cl.⁷ .................. C07D 211/70; C07D 211/82
(52) U.S. Cl. ......................... 546/350; 546/352
(58) Field of Search ................... 546/350, 352

(56) References Cited

FOREIGN PATENT DOCUMENTS

WO    WO 02/34720 A1    5/2002

OTHER PUBLICATIONS

Kuindzhi et al, Chemical Abstracts, vol. 68, No. 25, Jun. 17, 1968, Columbus, Ohio, US; abstract No. 114378, XP002267029, "6–Methyl–2–vinylpyridine" & Metody Polucheniy A Khimicheskikh Reaktivov I Preparatov (1967), No. 15, 93–5.

*Primary Examiner*—Cecilia J. Tsang
*Assistant Examiner*—Raymond Covington
(74) *Attorney, Agent, or Firm*—Nixon & Vanderhye, P.C.

(57) ABSTRACT

The present invention relates to a process for the preparation of 2,6-divinylpyridine and 2-methyl-6-vinylpyridine over modified zeolite catalysts. In particular, it relates to the method for the synthesis of 2,6-divinylpyridine and 2-methyl-6-vinylpyridine from 2,6-lutidine and formaldehyde in vapour phase in an eco-friendly method with high yield and selectivity. This invention provides a non-corrosive, eco-friendly process, where the catalyst can be reused for many times. 2,6-Divinylpyridine is useful stating material in polymer industry.

9 Claims, No Drawings

PROCESS FOR PREPARING 2,6-DIVINYLPYRIDINE AND 2-METHYL-6-VINYLPYRIDINE FROM 2,6-LUTIDINE OVER MODIFIED ZEOLITES

FIELD OF INVENTION

The present invention relates to a process for the preparation of 2,6-divinylpyridine and 2-methyl-6-vinylpyridine over modified zeolite catalysts. In particular, it relates to the method for the synthesis of 2,6-divinylpyridine and 2-methyl-6-vinylpyridine from 2,6-lutidine and formaldehyde in vapour phase in an eco-friendly method with high yield and selectivity. This invention provides a non-corrosive, eco-friendly process, where the catalyst can be reused for many times. 2,6-Divinylpyridine is useful starting material in polymer industry.

BACKGROUND OF THE INVENTION 2,6-Divinylpyridine is used in the preparation of an aminated ion-exchange resins containing divinyl substituted heterocyclic co-monomers as cross-linkers 2,6-Divinylpyridine (2,6-DVP) and 2-methyl-6-vinylpyridine (2M6VP) were synthesized by condensation of 2,6-lutidine and formaldehyde using potassium salts as catalysts. This method involves homogeneous conditions alongwith the high temperature and pressure [E.G. Martin, U.S. Pat. No. 2,824,844 (1958); Chem. Abstract.52 (1958) 9482i; J. Michalski, K. Studniarski, Roczniki Chem. 29 (1955) 1141; Chem. Abstract. 51 (1957) 10530c and Chem. Abstract 62 (1965) 1627c].

2,6-DVP and 2M6VP were also prepared by oxidative dehydrogenation of dialkyl heteroaromatics over $V_2O_5$/MgO and $MoO_3$/MgO catalysts in the presence of $O_2$ [I P. Belomestnykh, N. N. Rozhdestvenskaya, G. V. Isagulyants, Khim. Geterotsikl. Soedian. 6 (1994) 802; Chem. Abstract. 122 (1995) 31287r.].

We have reported the synthesis of 2-vinylpyridine and 4-vinylpyridine by side-chain alkylation of (2- and 4-methylpyridines) 2- and 4-picoline over modified basic zeolites. [Appl. Catal. (2003) in press].

OBJECTS OF THE INVENTION

The main object of the invention is to provide a process for the synthesis of 2,6-divinylpyridine and 2-methyl-6-vinylpyridine over modified zeolites in a heterogeneous eco-friendly method.

Another object of the invention is to provide a process for the preparation of 2,6-DVP and 2M6VP in high yield and high selectivity.

SUMMARY OF THE INVENTION

The present invention relates to develop a process for the preparation of 2,6-divinylpyridine and 2-methyl-6-vinylpyridine from 2,6-lutidine and formaldehyde in vapour phase over zeolite/ molecular sieve catalysts. The catalyst comprises of particularly ZSM-5 (pentasil family) with sodium, potassium, rubidium, cesium, magnesium, calcium, strontium and/or barium, etc cation or their species.

Accordingly, the present invention provides a process for the simultaneous production of 2,6-divinylpyridine and 2-methyl-6-vinylpyridine comprising reacting 2,6-lutidine with formaldehyde in a catalytic zone containing a modified zeolite catalyst, the temperature of the catalytic zone being in the range of 200 to 450° C., the reaction being carried out at a weight hourly space velocity in the range of 0.25 to 1.0 $h^{-1}$, the molar ratio of 2,6-lutidine to formaldehyde being 1:1 to 1:4.

In one embodiment of the invention, the modified zeolite catalyst comprises a modified ZSM-5 pentasil type zeolite catalyst, preferably modified by an alkali or alkaline earth metal ion selected from the group consisting of $Li^+$, $Na^+$, $K^+$, $Rb^+$, $Cs^+$, $Mg^{2+}$, $Ca^{2+}$, $Sr^{2+}$, $Ba^{2+}$.

In another embodiment of the invention, the modified ZSM-5 catalyst is a two cation modified ZSM-5, such as Cs—K-ZSM-5.

In yet another embodiment of the invention, the weight percent of the alkali or alkaline earth metal ion in ZSM-5 is in the range of 1 wt % to 4 wt %.

In yet another embodiment of the invention, the ZSM-5 catalyst is modified by potassium ion, the potassium ion source being selected from the group consisting of $KO^tBu$, KOH, KF, $KNO_3$, $K_3PO_4$ and KOAc, to improve the yield and selectivity of 2,6-divinylpyridine.

In a further embodiment of the invention, the modified zeolite is 3 wt % KZSM-5, calcined at a temperature in the range of 400° C. to 700° C.

In a further embodiment of the invention, the temperature of the catalytic zone is 300° C., the molar ratio of formaldehyde to 2,6-lutidine is 4:1 and the weight hourly space velocity in the process is 0.5 $h^{-1}$.

Another embodiment of the present invention provides a process for the preparation of 2,6-divinylpyridine and 2M6VP form 2,6-lutidine and formaldehyde in the presence of catalyst which comprises ZSM-5 containing one or two elements(s) from alkali and/or alkaline earth metal ions like $Na^+$, $K^+$, $Rb^+$, $Cs^+$, $Mg^{2+}$, $Ca^{2+}$, $Sr^{2+}$, $Ba^{2+}$ etc which can be reused for several times.

DETAILED DESCRIPTION OF THE INVENTION

The modified HZSM-5 catalyst was used in the development of the process. Each zeolite was pelleted without binder, crushed and sized 18–30 mesh before the impregnation. The ZSM-5 catalyst was modified by using required amount of alkali or alkaline earth cation nitrate by an impregnation method. In the case of potassium, different precursors like $KO^tBu$, KF, KOAc, $K_3PO_4$, $KNO_3$, or KOH were used to modify ZSM-5 ($SiO_2/Al_2O_3$=30) catalyst. The required amount of precursor was taken in the form of nitrate or other soluble salts in 30 ml of distilled water. 4.0 g of the meshed catalyst was added to it and kept for soaking for 12 h. Then it was dried at 110° C. over night and calcined at 420° C. for 4 h before using for the reaction.

In a typical procedure for the synthesis of $KO^tBu$ modified ZSM-5 (30) catalyst is as follows; 7 g of HZSM-5 (30) was taken in 250 ml two-necked round bottom flask. Prior to modification the catalyst was predried in oven at 100° C. for 1 h followed by flushing with nitrogen gas to remove water content present in the channels of the catalyst. In another round bottom flask required amount of $KO^tBu$ was dissolved in dry DMSO solvent. This solution was added to HZSM-5 (30) catalyst and kept stirring for 24 h in presence of nitrogen atmosphere. After 24 h stirring the resultant mixture was filtered, dried at 120° C. overnight and calcined at 400° C. for 4 h. the reactions were carried out in a fixed bed, continuous, down-flow pyrex reactor with internal diameter of 20 mm at atmospheric pressure. All the catalysts were activated by calcination in a flow of air at 420° C. for 4 h and brought to the reaction temperature in situ. A mixture of 2,6-lutidine and formaldehyde 37% wt/v was fed from a syringe pump at a rate of 2 ml. h$^{-1}$. The effluents from the reactor were cooled and periodically collected with an ice trap. The samples were analyzed by gas chromatography (SCHIMADZU-14B) fixed with an OV-17 (2 mm×⅛" OD) on chromosorb W-HP column and flame ionization detector. The carrier gas was N$_2$ (100 kpa) and the column temperature programme was 90° C. (5 min), 2° C. min$^{-1}$, 120° C. (10 min), 180° C. (injector) and 250° C. (detector). Products were confirmed by GC-Ms and NMR techniques. 2,6-DVP and 2M6VP arc formed as major products during side-chain alkylation of 2,6-lutidine and formaldehyde with all the catalysts studied here. Other products include 2-methyl-6-ethylpyridine and isomerized product 2,5-divinylpyridine.

The present invention will be explained in more detail by the following examples, which do not limit the scope of the invention in any way.

EXAMPLE 1

Synthesis of Potassium Modified ZSM-5.

Four grams of calcined HZSM-5 having SiO$_2$/Al$_2$O$_3$ molar ratio of 30 was taken in the form of 18–30 mesh size and soaked in 30 ml of the solution of potassium nitrate containing 0.4 g potassium for 12 h Then it was dried at 110° C. overnight and calcined at 420° C. for 4 h before using for the reaction.

EXAMPLE 2

Synthesis of Cesium Modified ZSM-5.

Same procedure as given in Example 1 was used for the preparation of other metal ion ZSM-5 catalyst by using their inorganic salts as precursors. Cesium nitrate was used for Cs-ZSM-5.

EXAMPLE 3

Modified ZSM-5 was used in the following reaction for the preparation of 2,6-divinylpyridine and 2-methyl-6-vinylpyridine. Cs-ZSM-5 (SiO2/Al2O3=30) (3 wt % Cs) catalyst was packed in a pyrex reactor having and inner diameter of 20 mm with the length of 30–40 cm and the catalytic zone was heated at 300° C. Then the mixture was fed from top of formaldehyde 2,6-lutidine=4:1 molar. The weight hourly space velocity was 0.5 h$^{-1}$. The liquid product selectivities for 2,6-divinylpyridine (2,6-DVP) and 2-methyl-6-vinylpyridine (2M6VP) were 25.2 and 74.8% at 37.1 wt % conversion of 2,6-lutidine (at time on stream (TOS)=6 h) respectively.

EXAMPLE 4

Conversion of 2,6-lutidine and formaldehyde was carried out over K-ZSM-5 (3 wt % K) at 300° C. with 0.5 h$^{-1}$ W.H.S.V. The catalyst was 4 g with 18–30 mesh size and feed rate of 2 ml. h$^{-1}$. 2,6-Lutidine to formaldehyde molar ratio was 1:4. The liquid product selectivities were 36.1 and 60.0 at 51,5 wt % conversion of 2,6-lutidine at TOS=6 h.

EXAMPLE 5

Reaction of 2,6-lutidine and formaldehyde was carried out over Rb-ZSM-5 (30) at 300° C. with 0.5 h$^{-1}$ W.H.S.V. The catalyst was 4 g with 18–30 mesh size and feed rate of 2 ml. h$^{-1}$. 2,6-Lutidine to formaldehyde molar ratio was 1:4. The liquid product selectivities of 2,6-divinylpyridine and 2-methyl-6-vinylpyridien were 39.4 and 60.6 wt % at 62.3 wt % conversion of 2,6-lutidine at TOS=6 h.

EXAMPLE 6

Reaction of 2,6-lutidine and formaldehyde was carried out over Na-ZSM-5 (SiO$_2$/Al$_2$O$_3$=30) at 300° C. with 0.5 h$^{-1}$ W.H.S,V The catalyst was 4 g with 18–30 mesh size and feed rate of 2 ml h$^{-1}$. The molar ratio of 2,6-lutidine to formaldehyde 1:4. The liquid product selectivities were 30.4 and 69.6% for 2,6-DVP and 2M6VP respectively, at 53.3 wt % conversion of 2,6-lutidine.

EXAMPLE 7

Reaction of 2,6-lutidine and formaldehyde was carried out over Sr-ZSM-5 (SiO$_2$/Al$_2$O$_3$=30 at 300° C. with 0.5 h$^{-1}$ W.H.S.V. The catalyst was 4 g with 18–30 mesh size and feed rate of 2 ml. h$^{-1}$. The molar ratio of 2,6-lutidine: formaldehyde was 1:4. The liquid product selectivities were 24.9 and 75.1% of 2,6-DVP and 2M6VP respectively, at 32.5 wt % conversion of 2,6-lutidine at TOS=6 h.

EXAMPLE 8

Reaction of 2,6-lutidine and formaldehyde was carried out over BaZSM-5 (30) at 300° C. with 0.5 h$^{-1}$ W.H.S.V. The catalyst was 4 g with 18–30 mesh size and feed rate of 2 ml. h$^{-1}$. The molar ratio of 2,6-lutidine: formaldehyde was 1:4. The liquid product selectivity was >98% of 2,6-DVP at 21.9% conversion of 2,6-lutidine at TOS=6 h.

EXAMPLE 9

Reaction of 2,6-lutidine and formaldehyde was carried out over Cs-K-ZSM-5 (SiO$_2$/Al$_2$O$_3$=30) at 300° C. with 0.5 h$^{-1}$ W.H.S.V. The catalyst was 4 g with 18–30 mesh size and feed rate of 2 ml. h$^{-1}$. The molar ratio of 2,6-lutidine; formaldehyde was 1:4. The liquid product selectivities were 31.0 and 67.8 wt % for 2,6-DVP and 2M6VP at 57.8 wt % conversion of 2,6-lutidine respectively, at TOS=6 h.

EXAMPLE 10

The reaction of 2,6-lutidine and formaldehyde was carried out over K-ZSM-5 (30, 3 wt % K) in the reaction temperature range of 250 to 400° C. The catalyst was 4 g with 18–30 mesh size and feed rate 2 ml h$^{-1}$. The molar ratio of 2,6-lutidine: formaldehyde was 1:4. The liquid product selectivities were 32.1% 2,6-DVP and 67.9% 2M6VP at 16.1 wt % conversion of 2,6-lutidine at 250° C. at TOS=6 h. The liquid product selectivities were 36.1% 2,6-DVP and 60.0% 2M6VP at 515 wt % conversion of 2,6-lutidine at 300° C. at TOS=6 h. The liquid product selectivities were 45.0% 2,6-DVP and 46.8% 2M6VP at 60.4 wt % conversion of 2,6-lutidine at 350° C. at TOS=6 h. The liquid product selectivities were 29.1% 2,6-DVP and 54.3% 2M6VP at 55.3 wt % conversion of 2,6-lutidine at 400° C. at TOS=6 h.

EXAMPLE 11

The reaction of 2,6-lutidine and formaldehyde was carried out over K-ZSM-5 (30, 3 wt % K) at 300° C. reaction temperature and W.H.S.V.=0.5 h$^{-1}$. The molar ratio of 2,6-lutidine: formaldehyde was varied in the range of 1:1 to 1:5. The catalyst was 4 g with 18–30 mesh size and feed rate 2 ml.h$^{-1}$. The liquid product selectivities were 30.9% 2,6-DVP and 68.9% 2M6VP at 39.3 wt % conversion of 2,6-lutidine for the molar ratio of lutidine: formaldehyde= 1:1. The liquid product selectivities were 36.1% 2,6-DVP and 60.0% 2M6VP at 51.5 wt % conversion of 2,6-lutidine for the molar ratio of lutidine: formaldehyde=1:4. The liquid product selectivities were 46.7% 2,6-DVP and 49.1%

2M6VP at 58.7 wt % conversion of 2,6-lutidine for the molar ratio of lutidine: formaldehyde=1:5.

EXAMPLE 12

The reaction of 2,6-lutidine and formaldehyde was carried out over K-ZSM-5 (30, 4 wt % K by ion exchange method) at 300° C. reaction temperature and weight hourly space velocity was varied in the range of 0.125 to 0.75 $h^{-1}$. The catalyst was 4 g with 18–30 mesh size and feed rate 2 ml.$h^{-1}$. The molar ratio of lutidine: formaldehyde was 1:4. The liquid product selectivities were 74.7% 2,6-DVP and 23.4% 2M6VP at 87.2 wt % conversion of 2,6-lutidine at 0.125 $h^{-1}$ and at TOS=5 h. The liquid product selectivities were 61.8% 2,6-DVP and 37.9% 2M6VP at 74.4 wt % conversion of 2,6-lutidine at TOS =6 h.

EXAMPLE 13

The calcination or activation temperature of the ZSM-5 catalyst was also varied in the temperature range of 420° C. to 700° C. The reaction of 2,6-lutidine and formaldehyde was carried out over KZSM-5 (30, 3wt %). The liquid product selectivities were 36.1% 2,6-DVP and 60.0% 2M6VP at 51.5 wt % conversion of 2,6-lutidine at TOS=6 h and calcination temperature was 420° C., 0.5 $h^{-1}$ W.H.S.V. The catalyst was 4 g with 18–30 mesh size and feed rate 2 ml.$h^{-1}$. The liquid product selectivities were 33.5% 2,6-DVP and 66.2% 2M6VP at 48.4 wt % conversion of 2,6-lutidine at TOS=5+6 h.

EXAMPLE 14

The weight percent potassium impregnated in the HZSM-5 catalyst was also varied from 1 wt % to 4 wt %. The reaction of 2,6-lutidine and formaldehyde was carried out over K-ZSM-5 (30) at 300° C. and 05 $h^{-1}$ W.H.S.V. The molar ratio of 2,6-lutidine: formaldehyde was 1:4. The weight of the catalyst was 4 g with 18–30 mesh size and feed rate 2 ml.$h^{-1}$. The liquid product selectivities were 24.3% 2,6-DVP and 75.7% 2M6VP at 34.0 wt % conversion of 2,6-lutidine at TOS=6 h and for 1 wt % KZSM-5. The liquid product selectivities were 61.8% 2,6-DVP and 379% 2M6VP at 74.4 wt % conversion of 2,6-lutidine at TOS=6 h for 4 wt % of potassium impregnation, KZSM-5.

EXAMPLE 15

The potassium precursor in the process of impregnation was also varied. The reaction of 2,6-lutidine and formaldehyde was carried out at 300° C. and 0.5 $h^{-1}$ W.H.S.V. The molar ratio of 2,6-lutidine: formaldehyde was 1:4. The weight of the catalyst was 4 g with 18–30 mesh size and feed rate 2 ml.$h^{-1}$. The molar ratio of 2,6-lutidine to formaldehyde was 1:4. The liquid product selectivities were 49.8% 2,6-DVP and 50.2% 2M6VP at 64.7 wt % conversion of 2,6-lutidine at TOS=6 h for KO$^t$Bu as a precursor. Similarly the following precursors were studied, KNO$_3$, KF, KOAc, K$_3$PO$_4$ and KOH. The conversion of 2,6-lutidine was varied from 51% to 80% with 36 to 56% of selectivity for 2,6-DVP.

We claim:

1. A process for the simultaneous production of 2,6-divinylpyridine and 2-methyl-6-vinylpyridine comprising reacting 2,6-lutidine with formaldehyde in a catalytic zone containing a modified zeolite catalyst, the temperature of the catalytic zone being in the range of 200 to 450° C., the reaction being carried out at a weight hourly space velocity in the range of 0.25 to 1.0 $h^{+1}$, the molar ratio of 2,6-lutidine to formaldehyde being 1:1 to 1:4, and wherein the modified zeolite catalyst comprises a modified ZSM-5 pentasil type zeolite catalyst, and wherein the modified zeolite catalyst is a ZSM-5 catalyst modified by an alkali or alkaline earth metal ion selected from the group consisting of Lit$^+$, Na$^+$, K$^+$, Rb$^+$, CS$^+$, Mg$^{2+}$, Ca$^{2+}$, Sr$^{2+}$, Ba$^{2+}$.

2. A process as claimed in claim 1 wherein the modified ZSM-5 catalyst is a two cation modified ZSM-5.

3. A process as claimed in claim 2 wherein the two cation modified ZSM-5 catalyst is Cs-K-ZSM-5.

4. A process as claimed in claim 1 wherein the weight percent of the alkali or alkaline earth metal ion in ZSM-5 is in the range of 1 wt % to 4 wt %.

5. A process as claimed in claim 1 wherein the ZSM-5 catalyst is modified by potassium ion, the potassium ion source being selected from the group consisting of KO$^1$Bu, KOH, KF, KNO$_3$, K$_3$PO$_4$ and KOAc, to improve the yield and selectivity of 2,6-divinylpyridine.

6. A process as claimed in claim 1 wherein the modified zeolite is 3 wt % KZSM-5, calcined at a temperature in the range of 400° C. to 700° C.

7. A process as claimed in claim 1 wherein the temperature of the catalytic zone is 300° C.

8. A process as claimed in claim 1 wherein the molar ratio of formaldehyde to 2,6-lutidine is 4:1.

9. A process as claimed in claim 1 wherein the weight hourly space velocity in the process is 0.5 $h^{+1}$.

* * * * *